(12) United States Patent
Schertiger et al.

(10) Patent No.: US 9,974,682 B2
(45) Date of Patent: May 22, 2018

(54) SECUREMENT OF COLLECTING BAGS FOR HUMAN BODY WASTES TO THE SKIN

(71) Applicant: Coloplast A/S, Humlebaek (DK)

(72) Inventors: Lars Olav Schertiger, Fredensborg (DK); Preben Luther, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 477 days.

(21) Appl. No.: 14/439,664

(22) PCT Filed: Oct. 28, 2013

(86) PCT No.: PCT/DK2013/050344
§ 371 (c)(1),
(2) Date: Apr. 30, 2015

(87) PCT Pub. No.: WO2014/067526
PCT Pub. Date: May 8, 2014

(65) Prior Publication Data
US 2015/0257922 A1    Sep. 17, 2015

(30) Foreign Application Priority Data

Nov. 2, 2012 (DK) .............................. 2012 70672

(51) Int. Cl.
*A61F 5/448* (2006.01)
*A61F 5/443* (2006.01)
*A61F 5/44* (2006.01)

(52) U.S. Cl.
CPC .............. *A61F 5/443* (2013.01); *A61F 5/448* (2013.01); *A61F 5/4408* (2013.01)

(58) Field of Classification Search
CPC ...................... A61F 5/44; A61F 5/4401; A61F 5/4404–5/441; A61F 5/442–5/4556; A61F 2005/4402; A61F 2005/4415; A61F 2005/4455; A61F 2005/4483; A61F 2005/4486; A61F 2005/4495
USPC .......................................... 604/332–345, 355
See application file for complete search history.

(56) References Cited

U.S. PATENT DOCUMENTS

| | | | | |
|---|---|---|---|---|
| 2,796,063 | A * | 6/1957 | Smelser | A61F 5/448 604/342 |
| 3,022,786 | A * | 2/1962 | Nalon | A61F 5/448 604/342 |
| 3,948,256 | A * | 4/1976 | Schneider | A61F 5/448 604/344 |
| 4,834,731 | A * | 5/1989 | Nowak | A61F 5/448 604/339 |
| 6,589,222 | B1 | 7/2003 | Olsen | |
| 2005/0261646 | A1 | 11/2005 | Wayne et al. | |

(Continued)

FOREIGN PATENT DOCUMENTS

| | | |
|---|---|---|
| CN | 1396816 A | 2/2003 |
| GB | 2311467 A1 | 10/1997 |

(Continued)

*Primary Examiner* — Susan Su
(74) *Attorney, Agent, or Firm* — Coloplast Corp., Coloplast A/S; Nick Baumann

(57) ABSTRACT

Disclosed is an anchoring element for engagement with a base plate for a collecting bag for human body wastes. Also disclosed is a kit for securing collecting bags for human body wastes to skin, comprising an anchoring element and an adhesive base plate and optionally a collecting bag for the human body wastes.

14 Claims, 6 Drawing Sheets

(56) References Cited

U.S. PATENT DOCUMENTS

| | | | |
|---|---|---|---|
| 2007/0005032 A1* | 1/2007 | Shan | A61F 5/448 604/342 |
| 2009/0312685 A1 | 12/2009 | Olsen et al. | |
| 2010/0145292 A1* | 6/2010 | Mayer | A61F 5/443 604/337 |
| 2011/0213321 A1 | 9/2011 | Fattman et al. | |
| 2014/0316360 A1* | 10/2014 | Ekfeldt | A61F 5/445 604/344 |
| 2015/0065971 A1* | 3/2015 | Goldsmith | A61F 5/448 604/342 |

FOREIGN PATENT DOCUMENTS

| | | |
|---|---|---|
| RU | 2220685 C1 | 1/2004 |
| WO | 9834573 A1 | 8/1998 |
| WO | 0154632 A1 | 8/2001 |
| WO | 2012079592 A1 | 6/2012 |

\* cited by examiner

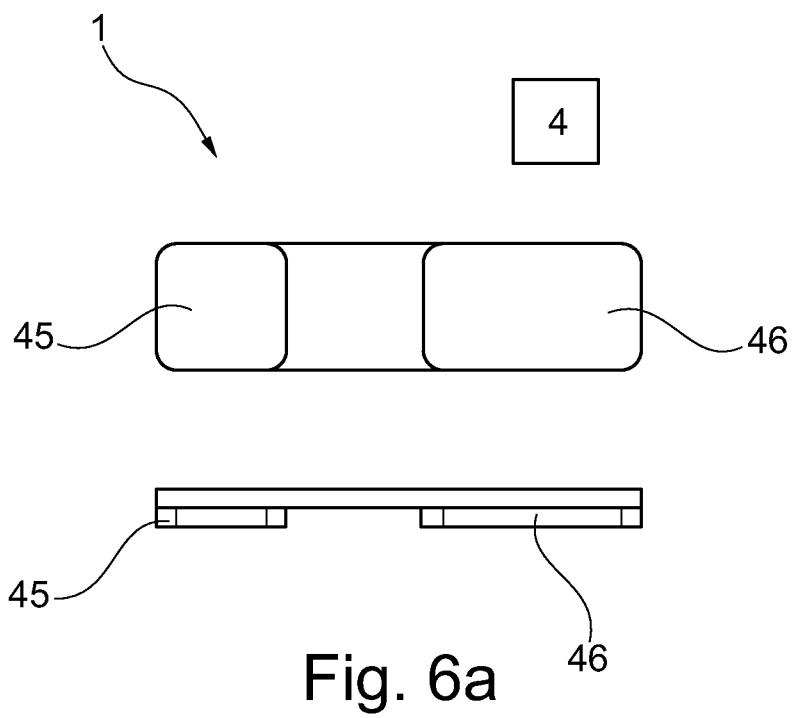
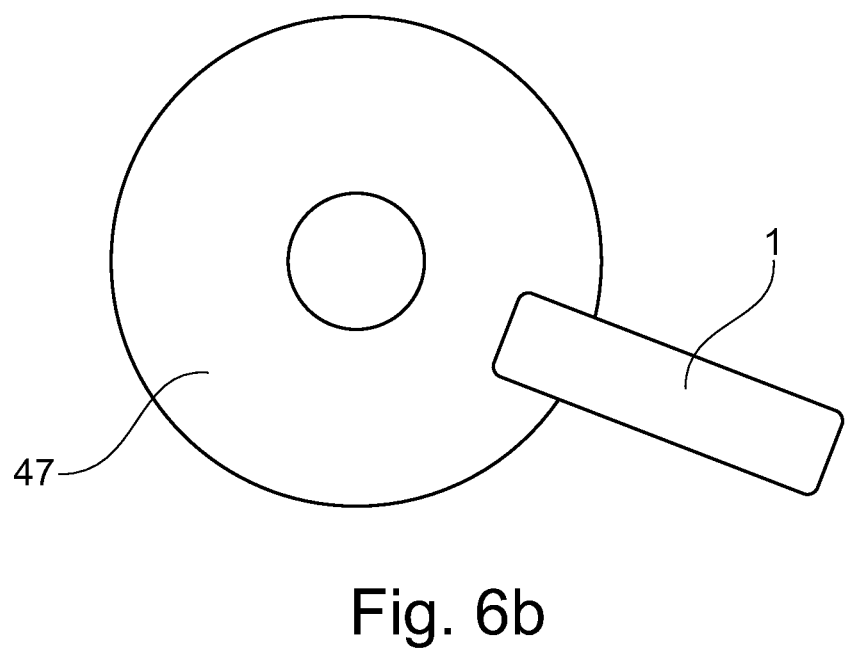
Fig. 6a
Fig. 6b

SECUREMENT OF COLLECTING BAGS FOR HUMAN BODY WASTES TO THE SKIN

The invention relates to securement of collecting bags for human body wastes to the human skin. In particular, the invention relates to an anchoring element for engagement with a base plate for a collecting bag for human body wastes. Furthermore, the invention relates to a kit for securing collecting bags for human body wastes to the human skin comprising an anchoring element and an adhesive base plate and optionally a collecting bag for the human body wastes.

BACKGROUND

In connection with surgery for a number of diseases in the gastro-intestinal tract, one of the consequences in many cases is that the patient is left with an abdominal stoma, or ostomy, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive base plate for attachment to the human skin. Alternatively, the ostomy appliance may be a two-piece appliance comprising a base plate and a collecting bag which may be coupled to and un-coupled from each other through a coupling means. This has the effect that the base plate does not need to be separated from the skin of the user as often as exchange of the collecting bag requires. The base plate may need only to be changed every 2-4 days depending on the user, whereas the collecting bag may be changed more than once per day. Typically, it is desirable to need as few exchanges of the base plate as possible in order to reduce the risk of skin complications.

A collecting bag for human body wastes usually comprises a front wall on the distal side and a rear wall on the proximal side. The walls are made of gas- and liquid impermeable foil-material (for example of polyethylene (PE), polyvinyl-chloride (PVC) or ethylene-vinyl-acetate (EVA)) that is welded around the edges or the rim so as to form a pouch defining a waste collection chamber. The bag may be welded only partly around the rim so that an opening for emptying the bag is provided at the bottom of the bag. In that case, the bag may be provided with means for closing that opening. The waste inlet opening is provided in the rear wall and placed in the upper part of the collecting bag so that when a user stands up, the waste inlet opening will be above the midline of the collecting bag. This leaves a larger collecting volume below the waste inlet opening. Thus, the top of the collecting bag is defined as the part closest to the waste inlet opening, and the bottom is defined as the opposite part.

One of the main concerns of ostomates using ostomy appliances having an adhesive base plate for attachment to the skin surrounding a stoma, and where a collecting bag is attached to the base plate for collecting stomal output, is that the ostomy adhesive attachment may be compromised resulting in sudden leakage or even complete detachment of the ostomy appliance which can be a stigmatising experience for the user.

Numerous attempts have been made to solve this problem and even though some attempts have been partly successful, still there exist no products which completely solve this problem. Two examples are given below.

GB2311467 describes an ostomy appliance comprising a pouch and an adhesive flange coupled to the pouch for securing the appliance with respect to the skin of a wearer. The adhesive flange has an aperture which communicates with an interior of the pouch and comprises a plurality of fingers which extend away from the aperture. The document also describes an adhesive flange for an ostomy appliance.

WO2012/052032 discloses an ostomy bag having an outer rotatable adhesive fitting wafer attached thereto. The solution offers a higher degree of customization to the user, as the user may cut the adhesive fitting wafer in such a way that it fits to the contour of the skin and the user may also rotate the ostomy bag relative to the wafer in order to achieve a desired orientation of the ostomy bag.

One reason why this problem is so difficult to solve is the fact that stomas and peoples anatomy are by definition highly individual. Different considerations need to be made for thin people than for larger people, for different skin types, for the position of the stoma which may vary a lot from person to person, for scar tissue surrounding the stoma, local irregular skin topography, e.g. hernias and wounds, and more—and in particular where combinations of some, or all of the above exist.

Thus, there is a need to further develop and find improvements in order to solve this problem. In other words, there exists a need to further customize or personalize ostomy appliances to fit the individual user's anatomy to increase the securement of the appliance to the skin surface.

The present invention provides the user with the possibility of improving the security of the attachment of the ostomy appliance to the skin and thus reduces the risk of sudden leakage and detachment of the appliance by facilitating an improved and differentiated, individually adapted attachment of the appliance.

SUMMARY OF THE INVENTION

The anchoring element according to the invention includes a flexible, elongatable member having a first and a second end, the first end engagable with a base plate and the second end attached to a component having an adhesive surface to be placed on the user's skin independently of the position of the base plate. Thus, the invention presents an anchoring element that allows the user to improve the secure attachment of the base plate for a collecting bag by anchoring the attachment of the base plate at a less problematic area of the skin surface of the user.

BRIEF DESCRIPTION OF THE DRAWING

FIG. 6a is a schematic view from below and from the side of another embodiment of the anchoring element of the invention, and FIG. 6b is a schematic top view of the anchoring element of the embodiment of FIG. 6a engaged with a base plate.

DETAILED DESCRIPTION OF THE INVENTION

Figure 1:
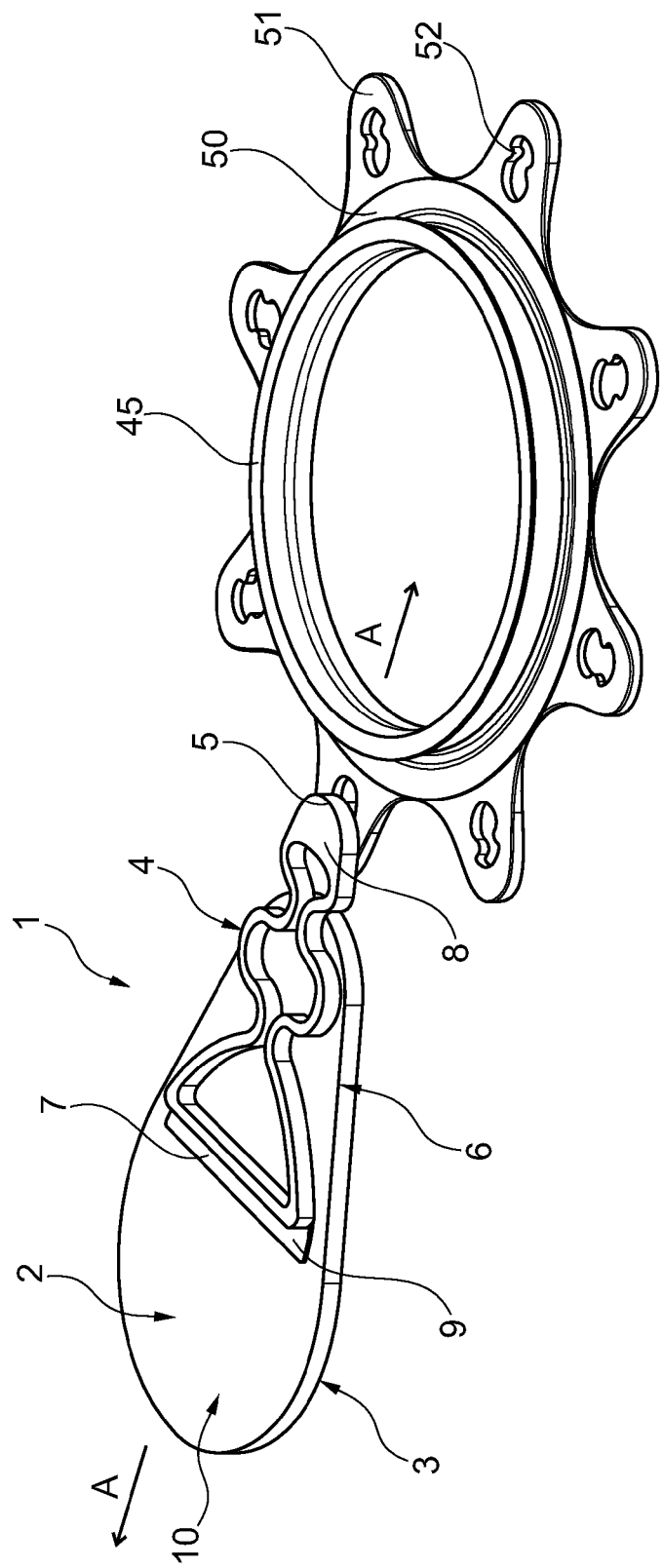
FIG. 1 is a perspective view of a first embodiment of an anchoring element according to the invention.

In a first aspect, the invention relates to an anchoring element for engagement with a base plate for a collecting bag for human body wastes comprising
  an attachment component having a proximal surface at least partly covered with skin friendly adhesive,
  a flexible member having a first end extending beyond an outer periphery of the attachment component and a second end attached to the attachment component, and wherein
  said first end of the flexible member comprises engagement means for engagement with the base plate.

Thereby, an anchoring element is obtained that allows the user to improve the secure attachment of the base plate for the collecting bag by anchoring the attachment of the base plate at a less problematic area of the skin surface of the user. In the present application, "anchoring element" should be interpreted as an element that at least aids in keeping a base plate for a collecting bag for human body wastes securely attached to the skin surface.

This is achieved by the fact that the skin friendly adhesive of the proximal surface of the anchoring element can be attached or adhered to the skin of the user at a skin surface location different from where the base plate itself is adhesively attached. Thereby, while the adhesive interface between the skin and the adhesive of the base plate is located in a problematic skin area, the adhesive interface between the proximal surface of the anchoring element and the user's skin can be placed in a non-problematic skin area (hereinafter referred to as a "normal skin" area or surface), the latter adhesive interface typically distanced further radially away from the centre of the base plate than an outer peripheral edge of the base plate.

Throughout this application, "distal surface" should be interpreted as a surface facing in a direction away from the skin of the user whereas a "proximal surface" should be interpreted as a surface facing in a direction towards the skin of a user. Furthermore, it shall be noted that the engagement between the anchoring element and the base plate according to the invention is intended to include both direct and indirect engagement, wherein direct engagement includes, e.g., that the engagement means of the flexible member engages with a surface of the base plate itself and wherein indirect engagement e.g. includes that the engagement means of the flexible member engages with an another element that is connected to the base plate e.g. a coupling ring as will be further explained in the description.

The anchoring element according to the invention at least provides both a high degree of freedom in selecting the position of attachment to the user's skin and a high level of convenience by being a separate part or entity that is independent of the other parts of the appliance, until it is applied in the use situation. Thereby, the improved secure attachment of the base plate is achieved without the anchoring element being a potentially obstructing extra device part that is in the way during application of the base plate to the skin surface, instead it may conveniently be engaged with the base plate after this has been correctly attached to the skin surface around the ostomy, to obtain a secure and individually customized secure attachment of the appliance.

More than one anchoring element may be applied or used to achieve the best and most secure attachment of the appliance to the individual user. This is further illustrated in the figures and in the detailed description.

As can be understood from the above, the fact that the securement of the appliance to the skin is improved with the anchoring element of the invention does not mean that the adhesive interface between the base plate and the user's skin is any less important than in an appliance without an anchoring element. The adhesive attachment between the base plate and the user's skin is still very important to maintain as best as possible since it provides several effects. One important effect is the maintenance of an appropriate seal between the stoma and the base plate to avoid the risk of the visceral contents of the stomal output attacking and potentially disintegrating the adhesive material on the skin-facing surface of the base plate.

Another important effect of the adhesive attachment between the base plate and the user's skin is, evidently, the ability to keep the appliance securely attached to the skin for a satisfactory product life-time. However, as it is well-known in the art, balancing the adhesive material characteristics between resistance to disintegration and strong and lasting adhesion capabilities necessitates a compromise in the adhesive material recipe. In other words: an adhesive material that is highly resistant to the stomal output often does not adhere so well to the skin, because it is typically harder and less flexible and thus does not penetrate into the small pores of the skin surface, whereas, by contrast, a softer and more flexible adhesive material that thus adheres well to the skin is often less resistant to stomal output.

The anchoring element of the invention also provides the possibility of providing a skin friendly adhesive with strong adhesion capabilities (flexible and able to penetrate into the pores of the skin) on the skin facing surface of the attachment component, while the adhesive material on the base plate can be provided having a strong resistance to the stomal output. Thereby it is understood that the anchoring element may comprise adhesive material that provides a major part of the attachment effect, whereas the adhesive material on the base plate only has to provide a minor or lesser part of the attachment effect of the appliance and may instead be made much more resistant to stomal output, however, thereby also being less flexible and pore-penetrating.

The attachment component of the anchoring element has a skin friendly adhesive layer held or disposed on a proximal surface of a layer of a backing or holding film such as, but not limited to, a polyethylene or polyurethane sheet material. Optionally, one or more further layers may be incorporated in the attachment component to provide additional effects. These may include, but are not limited to, absorbent and anisotropic material layers. The attachment component may have any suitable shape and size that makes it appropriate for use on an individual user, however not excluding that the component may also have standard dimensions. The extent of the attachment component is at least defined by an outer periphery.

The skin friendly adhesive of the attachment component may be disposed in such a way that it covers the whole of the proximal surface of the attachment component or at least covers a part thereof. Depending on the shape and size of the attachment component, it may be beneficial only to cover part of its proximal surface. The skin friendly adhesive of the attachment component may comprise adhesives of the type described in WO99/011302, but are of course not limited to these. It is well within the capabilities of the skilled person to provide an adhesive suitable to fulfil the requirements of the skin friendly adhesive of the attachment component.

The flexible member of the anchoring element is defined by having a first end extending beyond an outer periphery of the attachment component and a second end attached to the attachment component. In other words, a first end of the flexible member extends, or reaches, over a peripheral edge of the attachment component whereas a second end of the flexible member is attached to the attachment component. This includes, but is not limited to, embodiments wherein the second end of the flexible member is attached to a distal surface of the attachment component, or to a surface of the attachment component practically perpendicular to the skin facing surface or even to more than one of the surfaces. The distal surface of the attachment component may be a distal surface of the layer of the backing or holding film or an optional layer as described above. Here, "attached to" includes embodiments wherein the flexible member and the attachment component are fixedly attached which should be interpreted as being joined to each other in such a way, that they are not separable, at least not without destroying one or both parts. This joining may be done in any suitable manner e.g. by gluing or heat welding. The flexible member and the attachment component may also be integrally joined such as by being manufactured in a single process step from the same or different materials, e.g., integrally casted or alternatively moulded in an injection moulding process or may also comprise coating or layering one material with another, e.g., an adhesive. In alternative embodiments, "attached to" includes that the second end of the flexible member is releasably joined to the attachment component—however, in such embodiments, it should be ensured that the joint between the parts is able to transfer any moderate force applied to the flexible member without the parts being unintentionally released from each other.

As the flexible member is engaged with the base plate at the first end and attached to the attachment component at the second end, it provides the possibility of differentiating the positions of the adhesive interface between the attachment component and the skin and between the base plate and the skin, respectively, thereby increasing the degree of individual customization of secure attachment. In other words, the position of adhesive attachment of the proximal surface of the attachment component can be made independently of the position of the adhesive attachment of the base plate (subject to the flexibility and/or dimensions of the flexible member).

The first end of the flexible member comprises engagement means. The engagement means provide(s) for the engagement of the anchoring element to the base plate, either by direct or indirect engagement as previously mentioned. In a simple embodiment, the means can be a relatively small surface area integral with or fixedly joined to the first end of the flexible member suitable for holding a glue or adhesive. Here, "relatively small" should be interpreted as a surface area significantly smaller than the surface area of the base plate. Hereby, the engagement means may engage with the base plate, e.g., on the distal surface of a backing film of the base plate.

The engagement means may additionally or alternatively comprise any suitable kind and dimensions, e.g. taking the styles of different coupling types as inspiration. These coupling types may include hook-and-loop, snap, bayonet, press-fit and other perceivable styles. The engagement means may provide permanent engagement once engaged with the base plate or may be provided so as to also allow subsequent disengagement between the parts, e.g., for subsequent adjustment or repositioning.

In embodiments, the flexible member is primarily flexible in an axial direction defined by its first and second ends. This means that the flexibility of the flexible member is larger in the axial direction defined by the first and second ends of the flexible member than in the direction perpendicular thereto. Embodiments may include flexible members having flexibility in the axial direction of a factor two larger than in the direction perpendicular thereto. In other words, pulling the flexible member in the axial direction is easier than pulling it in the direction perpendicular to the axial direction. The flexibility of the flexible member will of course depend on material, shape and dimension parameters which will be apparent to the skilled person making a suitable flexible member according to the invention.

In embodiments, the flexible member comprises a spring means. This may include a traditional type coil-like spring made at least partly from metal and/or suitable polymer materials. The spring means may also comprise an injection moulded or cast element made from one or more suitable polymers, such as, but not limited to, polypropylene, and shaped so as to define a required force or elasticity as a measure for the flexibility. Examples may include a force of 0.5-10 N, such as 1-5 N and preferably approximately 2 N to elongate the flexible member (e.g. measured at a movement in the axial direction of approximately 10 mm of an endmost point of the first end of the flexible member in relation to where the second end of the flexible member is attached to the attachment component).

In other embodiments, the flexible member comprises an elastic band or tape. These may also include flexible films. Examples of the requirements for the elongation force of these embodiments may be equal to those mentioned above for the spring means embodiments. In these particular embodiments, the attachment component of the anchoring element may be formed by a layer of skin friendly adhesive at a second end of the flexible member and the engagement means may be formed by a suitable anchoring adhesive at a first end of the flexible member. Particularly, but not exclusively, the skin friendly and the anchoring adhesive are different adhesive types with characteristics making them suitable for their particular purposes as described previously. Thus, in these embodiments, the flexible member may be considered part of the elastic band or tape having a proximal surface that is not covered or surfaced by any of the adhesive types.

In embodiments, the flexible member comprises a hinge. The hinge may be placed anywhere on or along the extent of the flexible member, including at or adjacent to where the second end of the flexible member is attached to the attachment component, and at, or adjacent, the first end of the flexible member. The hinge may also be included as part of, or integrated with, the engagement means at the first end of the flexible member. Also, more than one hinge may be included depending on the requirements of the flexible member in order to, e.g., be suitable for an undulating or "hilly" topography of the skin surface of the user.

In embodiments, the flexible member further comprises an additional skin friendly adhesive on at least a part of a proximal surface. Applying a skin friendly adhesive on at least some of the proximal surface of the flexible member may be desirable. This may help to keep the flexible member close to the skin of the user, should any small bends arise in the flexible member, such that the flexible member does not protrude excessively from the surface of the skin, thus avoiding any visual indication of the flexible member through the clothes of the user. Secondly, the skin friendly adhesive may also aid in securing the whole appliance further to the skin of the user. The additional skin friendly adhesive may comprise any suitable type of adhesive and may for example be the same kind used for application to the skin facing surface of the attachment component.

In other embodiments, the additional skin friendly adhesive on the flexible member is a flexible adhesive. If the flexible member is attached partly or wholly to the skin surface, it may be beneficial that the additional skin friendly adhesive used is a flexible adhesive. In this regard, "flexible adhesive" should be interpreted as an adhesive that remains integral and does not detach or delaminate from the skin when the flexible member is submitted to, e.g., a moderate force in the axial or perpendicular direction. One such adhesive example can be found in publication WO2009/006901. In this application, "moderate force" should be interpreted as a force not exceeding those that may be expected to occur by the everyday body movements of the user, such as bending down to tie a shoe lace etc.

In embodiments, the engagement means are rotatable in relation to said base plate. In particular, but not exclusively, this includes the use of any suitable type of pivot link between the flexible member and the base plate. The rotatable engagement means may be able to rotate a full 360° or anything below. It is to be understood that even though the engagement means are described as being rotatable in relation to the base plate, alternative embodiments may also include that the pivot link is provided in the base plate and the engagement means of the flexible member simply engages therewith and unhindered follows any pivoting movement. As previously described with regard to the flexible member, a hinge may also form part of or be adjacent to the engagement means of the flexible member. Thereby, the link between the parts may not only be able to rotate or pivot in one plane, but may also be able to "bend", in order to be suitable for further aiding in the adaptation to any challenging topographies of the skin surface of the user.

In embodiments, at least a part of the flexible member is made from one or more materials selected from a group consisting of polymers, metals and/or rubber. In particular, a polypropylene based material is considered suitable as it is cost efficient both as a raw material and in process requirements while also having material characteristics making it easy to design a flexible member with the required flexibility. Two or more different polymers or any of the mentioned materials may be used for the flexible member if special individually defined characteristics are required.

In another aspect, the invention relates to a kit for securing collecting bags for human body wastes to the human skin comprising at least one anchoring element as described herein and an adhesive base plate and optionally a collecting bag for human body wastes.

Apart from being provided as a separate element according to the first aspect, the anchoring element may in this aspect of the invention be provided as part of a kit also comprising an adhesive base plate. The kit may further optionally comprise a collecting bag for human body wastes.

In this aspect, the anchoring element (particularly the engagement means of the flexible member) and the base plate may be provided with shape, form, kind and dimensions particularly suitable for immediate engagement between the parts. Also, in the case where a collecting bag is included, the collecting bag may of course be provided according to the requirements and wishes of the individual user.

In embodiments of the kit, the engagement means of the anchoring element attaches to a distal surface of the base plate. Thereby, the engagement means may directly contact "on top" of the distal surface of the base plate, typically the surface of the backing or holding film facing towards the collecting bag when the appliance is in use. As previously described, in embodiments, the engagement means may comprise a small adhesive surface which is particularly suited for attachment to a distal surface of the base plate. The position of attachment of the engagement means on the distal surface of the base plate is not limited to any particular radial distance from the stoma receiving opening in the base plate.

In other embodiments of the kit, the engagement means of the anchoring element attaches to coupling means for coupling to a collecting bag for human body wastes, said coupling means being fixedly joined to or integral with the base plate. The coupling means may comprise an annular coupling ring that is typically heat welded onto the distal surface, i.e. the backing or holding film of the base plate. Means may be provided integral with the coupling ring to engage with the engagement means of the flexible member of the anchoring element. In some examples, the means may be provided as one or more radially protruding loops, i.e. a flange of material integral with the coupling ring having a through-going hole in the flange to engage with, e.g., a pin-type engagement means on the flexible member.

In other embodiments of the kit, the engagement means of the anchoring element attaches to an element for controlling bending of the base plate at least partly:

layered within, embedded in the adhesive of, or attached to, said base plate.

Such an element for controlling bending of the base plate may include, but is not limited to, those described in WO 2012/079592. If the element for controlling bending is layered within the base plate, it means that it may be provided between two individual layers of the base plate, e.g., a backing film and an absorbent layer. If it is embedded in the adhesive of the base plate, it means that the element is surrounded by adhesive material on the major part of its external surface(s). Finally, if the element for controlling bending is attached to the base plate, it means that it may simply be attached to one of the distal or proximal surfaces of the base plate, e.g., by heat welding. Similar means for engagement with the engagement means of the flexible member as described above with regard to engagement with the coupling means may be provided on the element for controlling bending. In this regard, "at least partly" should be interpreted such that while a major part of the external surface(s) of the element for controlling bending may be layered within the base plate or embedded in the adhesive thereof, the element may comprise, e.g., one or more flanges extending out of the layer(s) of the base plate for meeting the engagement means of the flexible member.

In other embodiments of the kit, the engagement means of the anchoring element attaches to a multi-engagement member joined to a distal surface of the base plate. The multi-engagement member may be joined to the base plate by heat welding or gluing or any other suitable means. Alternatively, the multi-engagement member may be joined with the base plate in similar manners as described above with regard to the element for controlling bending. The multi-engagement member may be made from one or more suitable polymers, particularly polypropylene; the choice of materials should ensure a good joining effect between the member and the base plate. The multi-engagement member may be particularly suitable where more than one anchoring element are considered necessary to obtain the best and most secure attachment of the appliance to the skin surface. The multi-engagement member may accordingly comprise one or more means, such as protruding flanges with through-going holes therein, for engagement with the engagement means of the flexible member. These may be distributed over the multi-engagement member according to any suitable distribution scheme, including a symmetrical scheme. Additionally or alternatively, the multi-engagement member may also be attached to or made integral with the coupling means for the collecting bag in which case the engagement means of the first end of the flexible member engages with the means on the multi-engagement member. The coupling means, e.g., in the form of a coupling ring, will extend distally away from a distal surface of the multi-engagement member.

Combinations of two or more of the ways the engagement means of the flexible member and the base plate of the kit of the invention attaches to each other as described above, are also considered embodiments of the invention.

DETAILED DESCRIPTION OF THE DRAWING

FIG. 1 shows an anchoring element 1 according to the invention comprising an attachment component 2 and a flexible member 4. The flexible member 4 extends between a first end 5 and a second end 7 in an axial direction A-A thereof. The first end 5 of the flexible member 4 is extending beyond an outer periphery 6 of the attachment component 2 and the second end 7 is attached to the attachment component 2, in this figure shown as being attached by means of a flange 9 heat welded or glued to a distal surface 10 of the attachment component 2. A skin friendly adhesive (not shown) is at least partly covering the proximal surface 3 of the attachment component 2. The first end 5 of the flexible member 4 comprises engagement means 8 for engagement with a base plate for a collecting bag for human body wastes. In FIG. 1, the anchoring element 1 is engaged with a multi-engagement member 50 being made integral with coupling means in the form of a coupling ring 45 for coupling with a collecting bag (not shown). The multi-engagement member 50 has a number of radially protruding flanges 51 each having a through-going hole 52 therein providing corresponding means for engagement with the engagement means 8 of the flexible member 4. In the use situation, the multi-engagement member is joined to a base plate (not shown).

Figure 2:
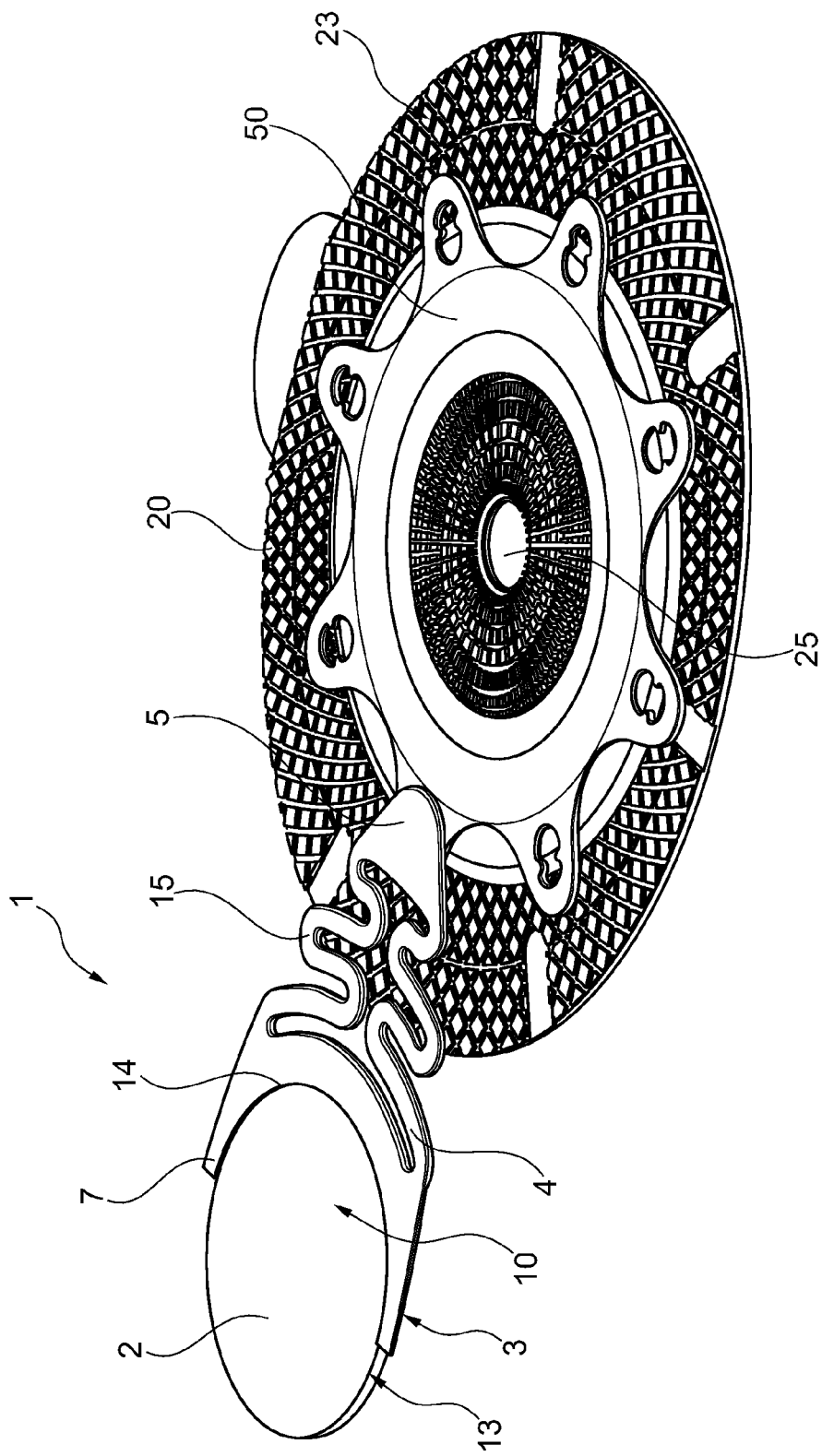
FIG. 2 is a perspective view of another embodiment of an anchoring element according to the invention.

FIG. 2 shows an alternative embodiment of an anchoring element 1 with an attachment component 2 and a flexible member 4. As in FIG. 1, the flexible member 4 is shown in the form of a spring means 15 having a higher flexibility in the axial direction A-A of the flexible member 4, than in the direction perpendicular thereto. Engagement means 8 (not visible in the figure) of the first end 5 of the flexible member 4 is engaged with a through-going hole 52 in a protruding flange 51 of the multi-engagement member 50. In FIG. 2 the multi-engagement member 50 is joined to a distal surface 23 of base plate 20 of an ostomy appliance and surrounding a stoma receiving opening 25 in the base plate 20. In FIG. 2, the second end 7 of the flexible member 4 is neither attached to the distal surface 10 nor to the proximal surface 3 of the attachment component 2, but instead to a surface 13 of the attachment component 2 being substantially perpendicular thereto (i.e. less than ten degrees deviation from the right angle). In FIG. 2, it is further shown that a crescent-shaped portion 14 of the second end 7 of the flexible member 4 abuts at least a part of the surface 13 constituting at least a part of an outer periphery of the attachment component 2. The crescent-shaped portion 14 of the second end 7 may be attached to the attachment component 2 over part, or the whole, of the abutting interface between the parts.

Figure 3:
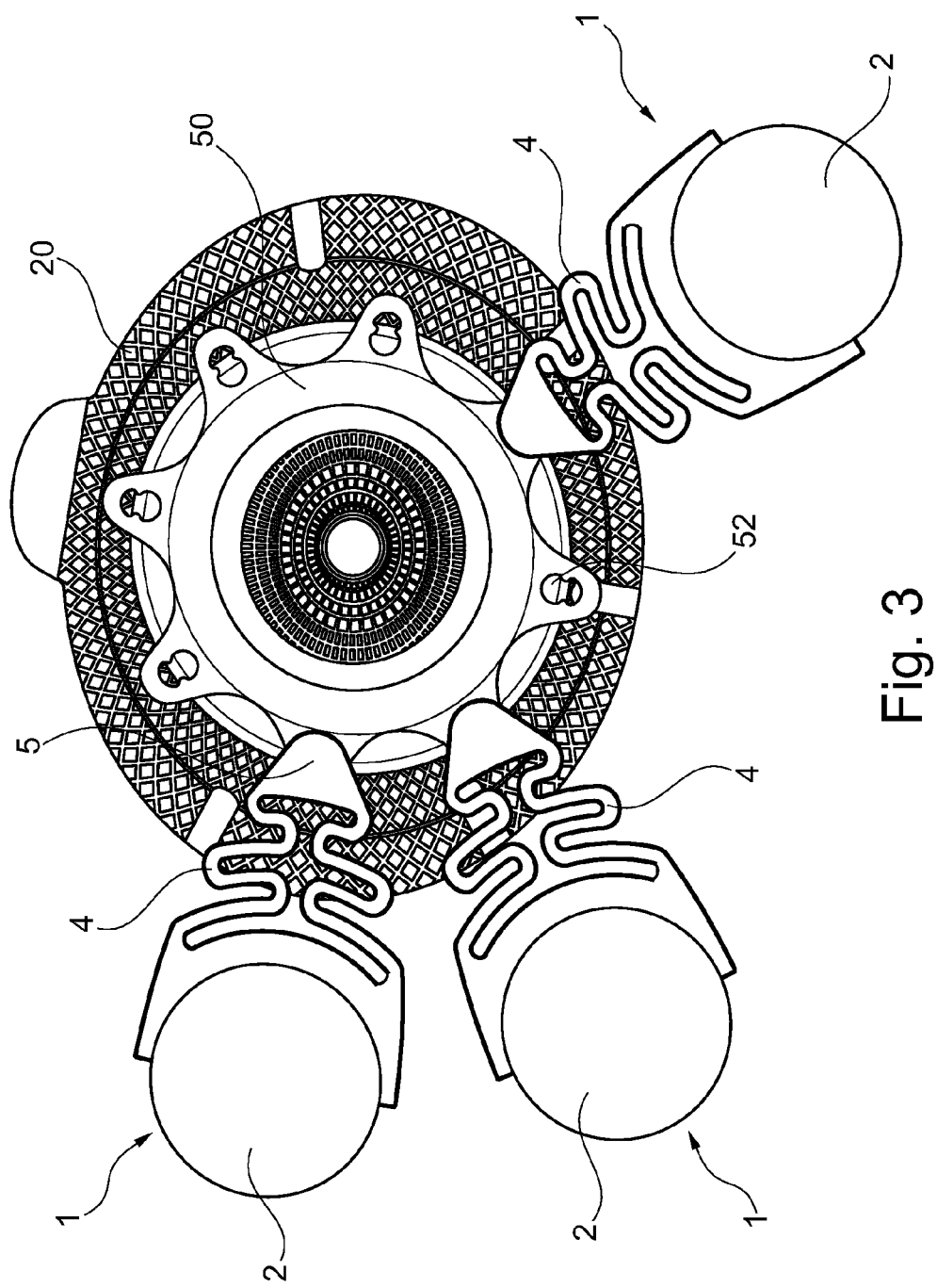
FIG. 3 is a plan view of a kit for securing collecting bags for human body wastes to the human skin according to another aspect of the invention.

FIG. 3 shows an anchoring element 1 similar to that of FIG. 2 and also engaged with a base plate 20 of an ostomy appliance by means of the multi-engagement member 50, only with the illustrated difference that three anchoring elements 1 are provided. As can be well understood from the figure, this arrangement provides the possibility of improving the securement of the base plate 20 to the user's skin (not shown) by using an appropriate number of anchoring elements that may be distributed on the user's skin in such a way that the attachment component 2 of the anchoring elements 1 may be adhered on to one or more normal skin areas. This is further facilitated by the flexibility in the axial direction of the flexible member 4 allowing for necessary elongation and/or retraction of the flexible element particularly, but not exclusively, needed when the user makes extreme body movements. As the figure further suggests, the engagement means 8 (not visible) of the first end 5 of the flexible member 4 may additionally be rotatable in relation to the base plate 20, since it engages with the through-going hole 52 shaped to allow a rotational movement of corresponding engagement means 8.

Figure 4:
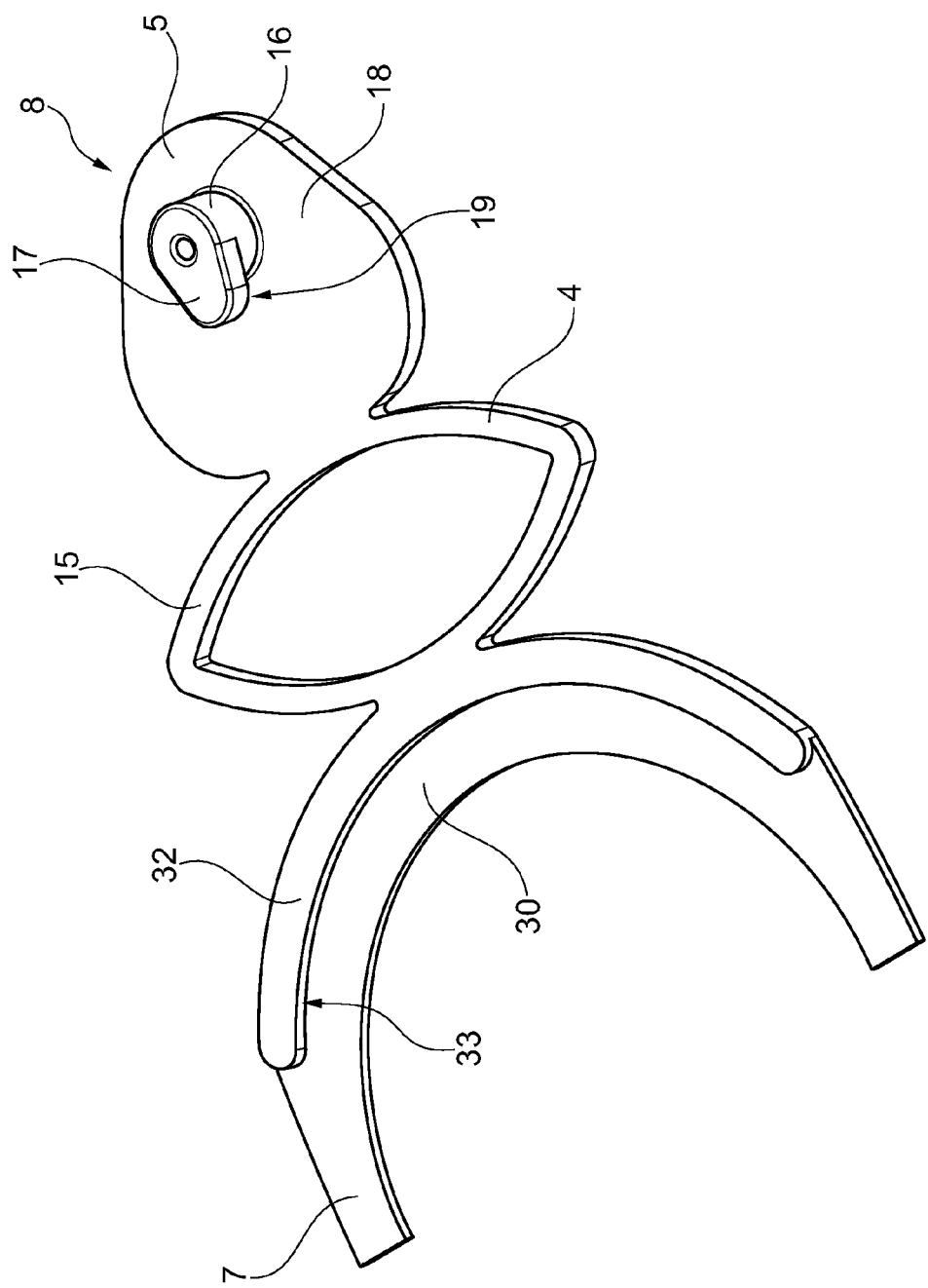
FIG. 4 is a perspective detailed view of a flexible member according to an embodiment of the invention.

FIG. 4 is a more detailed view of an alternative embodiment of the flexible member 4 also taking the form of a spring means 15. Engagement means 8 of the first end 5 of the flexible member 4 is shown in the form of a pin 16 extending perpendicularly from a proximal surface 18 constituting and/or being a part of the first end 5 of the flexible member 4. The engagement means 8 is further shown with a flange 17 at least partly extending beyond the diameter of the pin 16 and distanced from the proximal surface 18 to define a gap 19. With this particular arrangement of the engagement means 8, the engagement with the base plate 20 is achieved by pushing the pin 16 into and through the through-going hole 52 of the radially protruding flange 51 of the multi-engagement member 50 as shown in FIG. 3. Once put through, the flange 17 extending beyond the diameter of the pin 16 can be pulled a small distance in a direction parallel to flange 51 to "lock" the engagement means 8 in place in relation to the hole 52. The gap 19 then harbours a portion of the inner periphery of the hole 52.

Furthermore, FIG. 4 shows second end 7 of the flexible member having a first crescent-shaped surface 30 and an additional adjacent crescent-shaped surface 32. Surface 33 extends at least partly between surfaces 30 and 32 at substantially right angles thereto. This arrangement allows for the attachment of the second end 7 of the flexible member 4 to the attachment component 2 so that first crescent-shaped surface 30 joins to the distal surface 10 and second crescent-shaped surface 32 joins to the perpendicular surface 13 of the attachment component 2.

Figure 5:
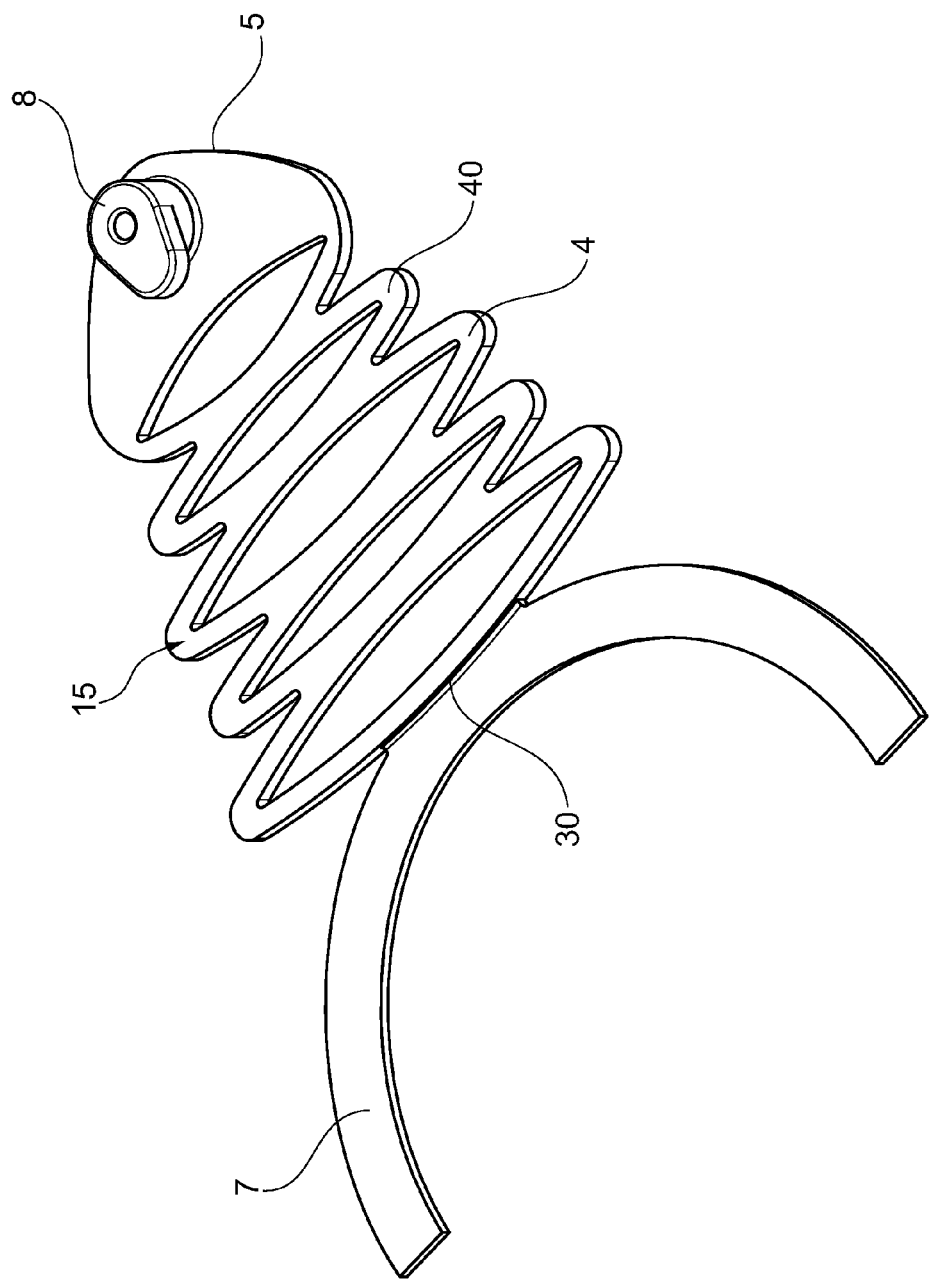
FIG. 5 is a perspective detailed view of a flexible member according to other embodiments of the invention.

FIG. 5 shows, as FIG. 4, a more detailed view of yet another embodiment of the flexible member 4 in the form of a spring means 15. In the figure, a single hinge 35 is provided in the flexible element 4, here shown bridging the second end 7 and the spring means 15. The hinge 35 is in the example provided as a section of the flexible member with a reduced thickness or with a recess in the material. It allows the second end 7 and the spring means 15 to be at angles with each other, e.g., in the case of an undulating skin topography. The flexible member 4 may of course comprise more than one hinge. The flexible element 4 has a proximal surface 40 (should be understood as the whole of the surface facing the reader when looking at the figure). Embodiments comprise that the whole or part of the proximal surface 40 comprises a skin friendly adhesive e.g. to keep the flexible element 4 from flexing unintentionally outward from the skin surface.

FIG. 6a shows another embodiment of an anchoring element 1 according to the invention, wherein the attachment component is a skin friendly adhesive 46 and the engagement means of the flexible element 4 is an anchoring adhesive 45.

FIG. 6b shows a plan view of the anchoring element 1 of the FIG. 6a embodiment, wherein the engagement means of the first end of the flexible member is engaged with a base plate and the attachment component of the second end of the flexible member is attached to the skin of a user (not shown). Furthermore, corresponding engagement means on the base plate may comprise a dedicated means such as, but not limited to, an anchoring zone 47 e.g. along an outer periphery of the base plate.

Finally, it is to be understood that not all perceivable embodiments within the scope, set out in the accompanying claims, have been illustrated. For example: the engagement means 8 of the flexible member 4 may in embodiments merely be a small adhesive surface engaging to attachment with the distal surface 23 of a base plate 20, thereby requiring no additional means in respect of the base plate.

The invention claimed is:

1. An anchoring element comprising:
   an elastic spring having a first end portion attachable to a base plate of an ostomy device and a second end portion connected to an adhesive patch, where the base plate of the ostomy device is attachable to skin surrounding a stoma and the adhesive patch is attachable to skin different from the skin surrounding the stoma; wherein the first end portion is mechanically attachable to the base plate of the ostomy device.

2. The anchoring element of claim 1, wherein the first end portion comprises a flange having a protruding pin, the pin configured to engage with the base plate.

3. The anchoring element of claim 1, wherein the first end portion is mechanically attachable in rotational engagement with the base plate of the ostomy device.

4. The anchoring element of claim 1, wherein the elastic spring includes a flange attached to the adhesive patch and opposed arms attached to the first end portion, with a void formed between the opposed arms.

5. The anchoring element of claim 1, wherein the elastic spring is more flexible along a longitudinal extent of the elastic spring than perpendicular thereto.

6. The anchoring element of claim 1, wherein the elastic spring comprises a hinge.

7. The anchoring element of claim 1, wherein the elastic spring comprises an adhesive on a portion of a proximal surface of the elastic spring.

8. The anchoring element of claim 1, wherein the elastic spring is made from one or more materials selected from a group consisting of polymers, metals and/or rubber.

9. The anchoring element of claim 1, wherein the first end portion of the elastic spring is configured to be permanently attached to the base plate.

10. A kit of parts for securing collecting bags for human body wastes to the human skin comprising an anchoring element according to claim 1, a base plate and a collecting bag for human body wastes.

11. The kit of parts of claim 10, wherein the first end portion of the elastic spring is attachable to a surface of the base plate not facing the skin of the user.

12. The kit of parts of claim 10, wherein the first end portion of the elastic spring is adapted to be attached to coupling means for coupling to the collecting bag for human body wastes, the coupling means being fixedly joined to or integral with the base plate.

13. The kit of parts according to claim 10, wherein the first end portion of the elastic spring is adapted to be attached to a multi-engagement member joined to a surface of the base plate not facing the skin of the user.

14. An anchoring element comprising:
   an elastic spring having a first end portion attachable to a base plate of an ostomy device and a second end portion connected to an adhesive patch, where the base plate of the ostomy device is attachable to skin surrounding a stoma and the adhesive patch is attachable to skin different from the skin surrounding the stoma; wherein the first end portion comprises a flange having a protruding pin, the pin configured to engage with the base plate.

* * * * *